United States Patent [19]

Lina et al.

[11] Patent Number: 5,144,056
[45] Date of Patent: Sep. 1, 1992

[54] FLUORINATED ACRYLIC MONOMERS AS HYDROPHOBIC AND OLEOPHOBIC AGENTS

[75] Inventors: Marie-Jose Lina, Tassin La Demi Lune; Andre Dessaint, Clermont, both of France

[73] Assignee: Atochem, Hauts-de-Seine, France

[21] Appl. No.: 323,100

[22] Filed: Mar. 14, 1989

Related U.S. Application Data

[63] Continuation of Ser. No. 932,807, Nov. 18, 1986, abandoned.

[30] Foreign Application Priority Data

Dec. 3, 1985 [FR] France .................. 85 17882

[51] Int. Cl.$^5$ ............................................. C07C 271/28
[52] U.S. Cl. ........................................ 560/25; 560/26; 525/920
[58] Field of Search ............................ 560/26, 25

[56] References Cited

U.S. PATENT DOCUMENTS

| | | | |
|---|---|---|---|
| 3,321,445 | 5/1967 | Lazerte et al. | 260/75 |
| 3,468,924 | 9/1969 | Gale | 260/453 |
| 3,503,915 | 3/1970 | Peterson | 260/29.2 |
| 3,528,849 | 9/1970 | Vullo et al. | 117/139.5 |
| 3,896,035 | 7/1975 | Schultz et al. | 252/8.75 |
| 3,896,251 | 7/1975 | Landucci | 428/290 |
| 4,024,178 | 5/1977 | Landucci | 260/472 |
| 4,199,526 | 4/1980 | Senet et al. | 558/280 |
| 4,321,404 | 3/1982 | Williams et al. | 560/115 |
| 4,335,138 | 6/1982 | Wiersdorff et al. | 558/280 |
| 4,482,608 | 11/1984 | Isbrandt et al. | 428/421 |
| 4,504,401 | 3/1985 | Matsuo et al. | 252/8.75 |
| 4,612,143 | 9/1986 | Piteau et al. | 558/280 |
| 4,788,287 | 11/1988 | Matsuo et al. | 560/25 |
| 4,920,190 | 4/1990 | Lina et al. | 560/26 |

FOREIGN PATENT DOCUMENTS

| | | |
|---|---|---|
| 1071225 | 3/1972 | Canada . |
| 895313 | 2/1980 | Canada . |
| 103752 | 3/1984 | European Pat. Off. . |
| 100227 | 8/1984 | European Pat. Off. . |
| 1620965 | 5/1970 | Fed. Rep. of Germany . |
| 2062244 | 6/1971 | France . |
| 512624 | 10/1971 | Switzerland . |
| 520813 | 3/1972 | Switzerland . |

*Primary Examiner*—Jose G. Dees
*Assistant Examiner*—B. Frazier
*Attorney, Agent, or Firm*—Pennie & Edmonds

[57] ABSTRACT

The invention relates to fluorinated acrylic monomers of the formula:

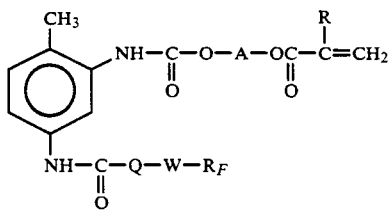

in which A and W denote divalent linkages, R is a hydrogen atom or a methyl radical, $R_F$ is a perfluoroalkyl radical and Q denotes an oxygen or sulphur atom or the group —NR'—, where R' denotes a hydrogen atom or an alkyl radical. Homo- or copolymers derived from these monomers are useful for the water or oil-repellent treatment of various substrates, particularly leather.

2 Claims, No Drawings

FLUORINATED ACRYLIC MONOMERS AS HYDROPHOBIC AND OLEOPHOBIC AGENTS

This is a continuation of application Ser. No. 06/932,807, filed Nov. 19, 1986, now abandoned.

TECHNICAL FIELD

The present invention relates to the field of fluorinated products intended for the water-repellent and oil-repellent treatment of substrates such as textiles, fitted carpets, wall coverings, wood, building materials, metals and plastics, and in particular, products which can be especially used for protecting leather, with finishing and maintenance characteristics such as flexibility, pleasant appearance and feel.

BACKGROUND ART

Use of fluorinated acrylic resins in these applications is well known, but has a number of disadvantages: slightly sticky feel, poor resistance to cleaning and abrasion, and slight modification of the appearance of the support.

Compositions comprising perfluorinated groups and urethane linkages have already been proposed; see, for example, U.S. Pat. 3,468,924, 3,503,915, 3,528,849, 3,896,035, 3,896,251 and 4,024,178, French Patent 2,062,244, German Patent 1,620,965, Canadian Patent 1,071,225, European Patent 103,752 and Swiss Patents 520,813 and 512,624. Unfortunately, these products do not always prove satisfactory, either because the synthesis of the intermediates is difficult, or because they have to be combined with acrylic copolymers since they are not film-forming, do not withstand dry cleaning and/or do not have good stain-repellent properties, or alternatively because they have to be supplied as an aqueous emulsion as a result of their low solubility in solvents.

To prevent the transfer of the printing powder during the preparation of transparencies by an electrographic process, the use of fluorinated polymers containing urethane groups has been proposed in European Patent 100,227. In particular, polymers derived from the fluorinated diurethane of the following formula are described in this patent:

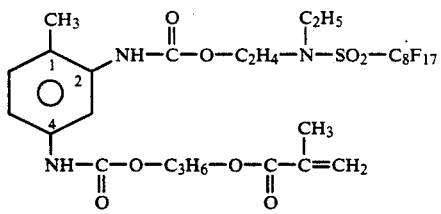

However, the polymers obtained from the fluorinated diurethane (I) have the disadvantage of forming insoluble gels or providing inadequate performance as regards their hydrophobic and oleophobic properties.

It has now been found, quite unexpectedly, that this disadvantage can be remedied by using a fluorinated urethane in which the polyfluorinated chain is bound at position 4 and not at position 2 as in the compound of formula (I) according to European Patent 100,227. The polymers derived from these diurethanes having a polyfluorinated chain at position 4 show good solubility in the usual solvents; they have excellent hydrophobic and oleophobic properties and are, in particular, entirely suitable for treating leather.

The subject of the present invention is, first, as fluorinated acrylic monomers, the diurethanes of general formula:

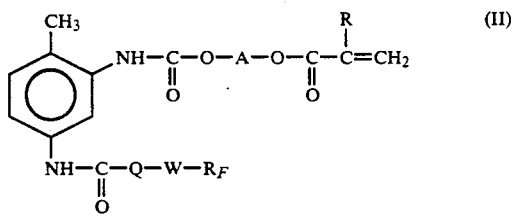

in which:

$R_F$ denotes a perfluoroalkyl radical having a straight or branched chain and containing from 2 to 20 carbon atoms (preferably 4 to 16), R denotes hydrogen or, preferably, a methyl radical, A denotes a divalent linkage which has 2 to 9 carbon atoms and can contain one or more oxygen atoms, Q denotes an oxygen or sulphur atom or the group —NR'—, where R' denotes hydrogen or an alkyl radical containing 1 to 4 carbon atoms, and W denotes a divalent linkage linked to Q through a carbon atom and capable of containing one or more oxygen, sulphur and/or nitrogen atoms.

The fluorinated acrylic monomers of formula (II) according to the invention can be prepared by reacting, in a first stage, toluene 2,4-diisocyanate with a substantially equimolar amount of a polyfluorinated compound of formula:

$$R_F—W—Q—H \qquad (III)$$

to form a fluorinated urethane-isocyanate of formula:

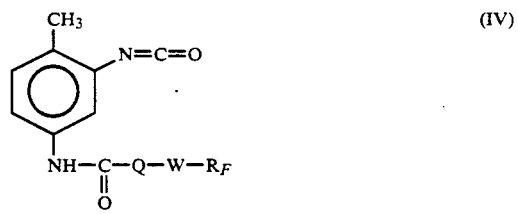

and then reacting this urethane-isocyanate with a substantially equimolar amount of an acrylic ester of formula:

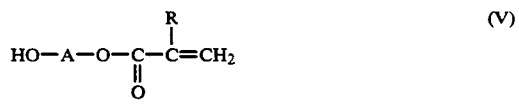

The polyfluorinated compound (III) is a compound containing a mobile hydrogen atom in the form of a terminal hydroxyl, thiol or primary or secondary amino group linked to the perfluoroalkyl radical through an alkylene bridge directly or via a sulphonamido, carboxamido, ether, thioether, sulfonyl or carboxylic ester group.

As examples of such polyfluorinated compounds, there may be mentioned more especially those of formulae:

$$R_F—(CH_2)_p—OH \qquad \text{(III-a)}$$

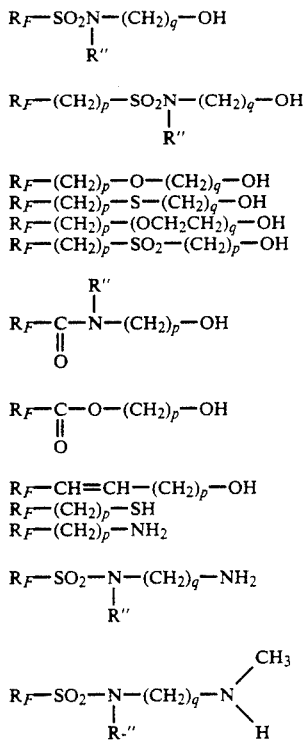

$$R_F\text{—}SO_2N\text{—}(CH_2)_q\text{—}OH \quad \text{(III-b)}$$
$$\phantom{R_F\text{—}SO_2N\text{—}}|\phantom{(CH_2)_q\text{—}OH}$$
$$\phantom{R_F\text{—}SO_2N\text{—}}R''$$

$$R_F\text{—}(CH_2)_p\text{—}SO_2N\text{—}(CH_2)_q\text{—}OH \quad \text{(III-c)}$$
$$\phantom{xxxxxxxxxxxxxxxxx}|$$
$$\phantom{xxxxxxxxxxxxxxxxx}R''$$

$$R_F\text{—}(CH_2)_p\text{—}O\text{—}(CH_2)_q\text{—}OH \quad \text{(III-d)}$$
$$R_F\text{—}(CH_2)_p\text{—}S\text{—}(CH_2)_q\text{—}OH \quad \text{(III-e)}$$
$$R_F\text{—}(CH_2)_p\text{—}(OCH_2CH_2)_q\text{—}OH \quad \text{(III-f)}$$
$$R_F\text{—}(CH_2)_p\text{—}SO_2\text{—}(CH_2)_p\text{—}OH \quad \text{(III-g)}$$

$$\begin{array}{c}R''\\|\\R_F\text{—}C\text{—}N\text{—}(CH_2)_p\text{—}OH\\\|\\O\end{array} \quad \text{(III-h)}$$

$$R_F\text{—}C\text{—}O\text{—}(CH_2)_p\text{—}OH \quad \text{(III-i)}$$
$$\phantom{xx}\|$$
$$\phantom{xx}O$$

$$R_F\text{—}CH=CH\text{—}(CH_2)_p\text{—}OH \quad \text{(III-j)}$$
$$R_F\text{—}(CH_2)_p\text{—}SH \quad \text{(III-k)}$$
$$R_F\text{—}(CH_2)_p\text{—}NH_2 \quad \text{(III-l)}$$

$$R_F\text{—}SO_2\text{—}N\text{—}(CH_2)_q\text{—}NH_2 \quad \text{(III-m)}$$
$$\phantom{xxxxxxx}|$$
$$\phantom{xxxxxxx}R''$$

$$R_F\text{—}SO_2\text{—}N\text{—}(CH_2)_q\text{—}N\begin{array}{c}CH_3\\ \\H\end{array} \quad \text{(III-n)}$$
$$\phantom{xxxxxxx}|$$
$$\phantom{xxxxxxx}R''$$

in which $R_F$ and $R''$ have the same meanings as above, and the symbols p and q, which may be identical or different, each denote an integer ranging from 1 to 20 and preferably equal to 2 or 4. For economical and practical reasons, it is especially advantageous to use a mixture of compounds in which different radicals $R_F$ are represented.

Among the compounds (III), those of formulae (III-a), (III-c) and (III-k), in which p and q are equal to 2, are especially preferred.

As examples of esters of formula (V), there may be mentioned, more especially, monoacrylates and monomethacrylates of diols or of polyalkylene glycols, such as ethylene glycol, propylene glycol, 1,3-propanediol, butanediols, 3-phenoxy-1,2-propanediol and triethylene glycol. Ethylene glycol monomethacrylate is preferably used.

The synthesis of the fluorinated acrylic monomers (II) according to the invention can be performed in an organic solvent, for example ketonic solvents such as methyl ethyl ketone or methyl isobutyl ketone, esters such as ethyl acetate or butyl acetate, aromatic solvents such as toluene, alkanes such as hexane, heptane or cyclohexane, ethers such as diisopropyl ether or tetrahydrofuran, halogenated solvents such as 1,1,1- trichloroethane or trichlorotrifluoroethane, and also dimethylformamide and N-methylpyrrolidone.

The addition reactions of the polyfluorinated compound $R_F\text{—}W\text{—}Q\text{—}H$ and the acrylic ester (V) to the —N=C=O groups are performed at between 30° and 90 C under an inert atmosphere, for example under anhydrous nitrogen. Since the addition of the polyfluorinated compound is slow, it is preferable to work in the presence of a catalyst, such as, for example, a tertiary amine such as triethylamine, triethylenediamine and N-methylmorpholine, a tin salt such as dibutyltin dilaurate and tin octoate or a lead salt such as lead naphthenate, this catalyst being used in the proportion of 0.05 to 1% relative to the total weight of the reagents and introduced with either of the reagents or boch.

In order to limit the concomitant formation of symmetrical diaddition products, that is to say products of the formulae:

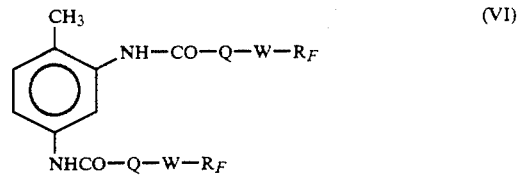

and

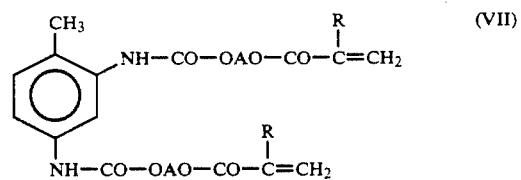

it is preferable to add the polyfluorinated compound (III) slowly, under conditions of dilution and temperature such that the reaction is virtually instantaneous and that there is always an excess of toluene diisocyanate relative to compound (III). Although it is not possible to completely prevent the formation of symmetrical diaddition products, the presence of these products in the solutions of acrylic monomers (II) which are intended for polymerization does not cause interference. It is, however, possible, if so desired, to remove them by fractional crystallization and filtration, since they are less soluble in solvents than the monomers (II).

Instead of using pure 2,4-toluene diisocyanate, which is very expensive, it is economically advantageous to use a technical grade toluene diisocyanate which can contain up to approximately 35% by weight (preferably up to approximately 20%) of the 2,6-isomer. In effect, insofar as their proportion remains relatively low, the presence of products of addition to this 2,6-isomer does not cause disadvantages for the applications in question.

The subject of the invention is also the polymers containing units of formula:

$$\begin{array}{c}CH_3\\ \\ \\ \text{Ph}\begin{array}{c}NH\text{—}C\text{—}O\text{—}A\text{—}OC\text{—}C\text{—}CH_2\text{—}\\\|\phantom{xxxxx}\|\phantom{x}|\\O\phantom{xxxxx}O\phantom{x}R\end{array}\\ \\NH\text{—}C\text{—}Q\text{—}W\text{—}R_F\\\|\\O\end{array} \quad \text{(VIII)}$$

in which the various symbols have the same meanings as above. These polymers can be obtained from the monomers of formula (II) by homopolymerization or by copolymerization with other monomers, fluorinated or otherwise, in a proportion ranging 1 up to 90% by weight (preferably up to approximately 50%) relative to the total weight of monomers.

As examples of comonomers which can be used in the context of the present invention, the following may be mentioned:

lower olefinic hydrocarbons, halogenated or otherwise, such as ethylene, propylene, isobutene, 3- chloro-1-isobutene, butadiene, isoprene, chloro- and dichlorobutadienes, fluoro- and difluorobutadienes, 2,5-dimethyl-1,5-hexadiene, diisobutylene; vinyl, allyl or vinylidene halides, such as vinyl or vinylidene chloride, vinyl or vinylidene fluoride, allyl bromide, methallyl chloride;

styrene and its derivatives, such as vinyltoluene, α-methylstyrene, α-cyanomethylstyrene, divinylbenzene, N-vinylcarbazole; vinyl esters such as vinyl acetate, vinyl propionate, the vinyl esters of the acids known commercially by the name "Versatic acids", vinyl isobutyrate, vinyl senecioate, vinyl succinate, vinyl isodecanoate, vinyl stearate, divinyl carbonate;

allyl esters such as allyl acetate and allyl heptanoate;

alkyl vinyl or alkyl allyl ethers, halogenated or otherwise, such as cetyl vinyl ether, dodecyl vinyl ether, isobutyl vinyl ether, ethyl vinyl ether, 2-chloroethyl vinyl ether, tetra allyloxyethane; vinyl alkyl ketones such as vinyl methyl ketone; unsaturated acids, for example acrylic, methacrylic, α-chloroacrylic, crotonic, maleic, fumaric, itaconic, citraconic and senecioic acids, their anhydrides and their esters such as vinyl, allyl, methyl, butyl, isobutyl, hexyl, heptyl ethyl-2-hexyl, cyclohexyl, lauryl, stearyl and 1-alkoxyethyl acrylates and methacrylates, dimethyl maleate, ethyl crotonate, acid methyl maleate, acid butyl itaconate, glycol or polyalkylene glycol diacrylates and dimethacrylates, such as ethylene glycol or triethylene glycol dimethacrylate, dichlorophosphatoalkyl acrylates and methacrylates such as dichlorophosphatoethyl methacrylate, and also acid bis(methacryloyloxyethyl) phosphate and methacryloyloxypropyltrimethoxysilane; acrylonitrile, methacrylonitrile, 2-chloroacrylonitrile, 2-cyanoethyl acrylate, methyleneglutaronitrile, vinylidene cyanide, alkyl cyanoacrylates such as isopropyl cyanoacrylate, trisacryloylhexahydro-s-triazine, vinyltrichlorosilane, vinyltrimethoxysilane, vinyltriethoxysilane, N-vinyl-2-pyrrolidone;

allyl alcohol, allyl glycolate, isobutenediol, allyloxyethanol, o-allylphenyl, divinylcarbinol, glycerol allyl ether, acrylamide, methacrylamide, maleamide and maleimide, N-(cyanoethyl)acrylamide, N-isopropylacrylamide, diacetoneacrylamide, N-(hydroxymethyl)acrylamide and -methacrylamide, N-(alkoxymethyl)acrylamides and methacrylamides, glyoxal bisacrylamide, sodium acrylate or methacrylate, 2-sulphoethyl acrylate, vinylsulphonic and styrene-p-sulphonic acids and their alkali metal salts, 3-aminocrotono- nitrile, monoallyl amine, vinylpyridines, glycidyl acrylate or methacrylate, allyl glycidyl ether, acrolein, N,N-dimethylaminoethyl or N-tert-butylamino ethyl methacrylate;

the unsaturated fluorine esters of the general formula:

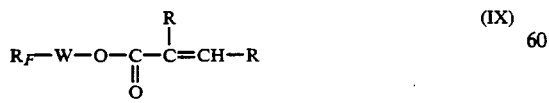

in which $R_F$, R and W have the same meanings as above.

These comonomers can be prepared according to known processes, for example by esterification of the corresponding polyfluorinated alcohols of formula:

by means of an alkenemonocarboxylic acid of formula:

$$HO-\underset{\underset{O}{\|}}{C}-\underset{\underset{}{\overset{R}{|}}}{C}=CH-R \qquad (XI)$$

such as, for example, acrylic acid, methacrylic acid or crotonic acid, in the presence of a catalyst such as sulphuric acid or p-toluenesulphonic acid. Instead of the acids of formula (XI), it is also possible to use their esters, anhydrides or halides. As examples of polyfluorinated alcohols of formula (X), there may be mentioned more especially those of formulae (III-a) to (III-j) above.

By way of comonomers which can be used in the context of the present invention, the following may also be mentioned:

the products of formula (VII) above;

the unsaturated esters of formula:

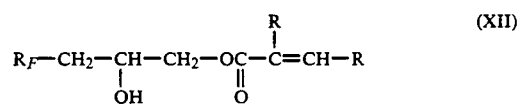

obtained by condensation of a fluorinated epoxide:

with an alkenemonocarboxylic acid of formula (XI);

the acrylates and methacrylates of ethers of polyethylene glycols or polypropylene glycols of formula:

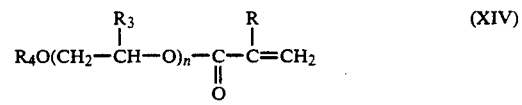

in which $R_3$ denotes a hydrogen atom or a methyl radical, $R_4$ denotes an alkyl radical and n is an integer between 2 and 10; and the compounds of formula:

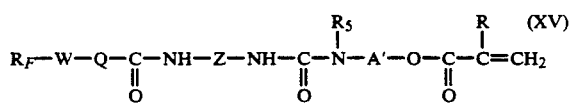

in which the symbols Q, R, $R_F$ and W have the same meanings as above, A' denotes an alkylene group having 2 or 3 carbon atoms, $R_5$ denotes an alkyl, cycloalkyl or piperazinyl radical, and Z denotes an aliphatic, cycloaliphatic or aromatic divalent linkage.

These compounds, which form the subject of a U.S. application Ser. No. 920,105, filed Oct. 16, 1986, which claims priority to French Patent Application No. 85/15,347 filed on Oct. 16, 1985, can be prepared by reacting substantially equimolar amounts of a polyfluorinated compound of formula (III) and an acrylic ester containing a secondary amino group, of formula:

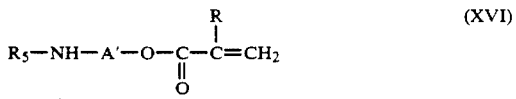

(XVI)

with an aliphatic, cycloaliphatic or aromatic diisocyanate, under working conditions similar to those described above for the preparation of the monomers (II).

Among the abovementioned comonomers, more special preference is given to simple alkyl acrylates and methacrylates or those containing a hydroxyl, amino or sulphonic acid functional group, the fluorinated compounds (IX) and (XV), methacrylates of polyethylene glycol ethers, vinyl ethers, vinyl or vinylidene chloride and fluoride, vinyl pyrrolidone, acrylamide and its derivatives, and acrylic or methacrylic acid.

The fluorinated polymers according to the invention can be prepared in a manner known per se, by polymerization in an organic solvent or in an aqueous emulsion, at a temperature which can range from room temperature to the boiling point of the reaction medium. It is preferable to work at between 70° and 110° C. The total concentration of the monomers can vary from 5 to 60% by weight.

The polymerization in a solvent medium can be carried out in ketonic solvents (for example acetone, methyl ethyl ketone, methyl isobutyl ketone), alcohols (for example isopropanol), esters (for example ethyl acetate or butyl acetate), ethers (for example diisopropyl ether, ethylene glycol ethyl or methyl ether, tetrahydrofuran, dioxane), aliphatic or aromatic hydrocarbons, halogenated hydrocarbons (for example perchloroethylene, 1,1,1-trichloroethane, trichlorotrifluoroethane), dimethylformamide or N-methyl-2 pyrrolidone.

The polymerization is performed in the presence of one or more initiators, which can be used in the proportion of 0 1 to 1.5% relative to the total weight of the monomers involved. As initiators, peroxides can be used, such as, for example, benzoyl peroxide, lauroyl peroxide, succinyl peroxide and tert-butyl perpivalate, or azo compounds such as, for example, 2,2,-azobisisobutyronitrile, 4,4,-azobis(4-cyanopentanoic acid) and azodicarbonamide. It is also possible to work in the presence of UV radiation and photoinitiators such as benzophenone, 2-methylanthraquinone or 2 chlorothioxanthone. The length of the polymeric chains can, if so desired, be adjusted by means of chain transfer agents such as alkyl mercaptans, carbon tetrachloride or triphenylmethane, used in the proportion of 0.05 to 0.5% relative to the total weight of monomers.

The polymerization in aqueous emulsion can be carried out according to well-known techniques, in discontinuous or continuous fashion. The surfactants to be used for the emulsification can be cationic, anionic or nonionic, according to the ionic nature desired for the final latex, and are preferably chosen from the best oil-in-water emulsifers which are as little wetting as possible. Cationic/nonionic or anionic/nonionic surfactant systems are preferably used. As examples of surfactants which can be used, the following may be mentioned more especially:

in the cationic series, long-chain tertiary amine salts such as N,N-dimethyloctadecylamine acetate, and the quaternary ammonium salts of fatty amines such as trimethylcetylammonium bromide or trimethyldodecylammonium chloride;

in the anionic series, alkali metal salts of long-chain alkylsulphonic acids and alkali metal arylalkyl sulphonates;

in the nonionic series, condensation products of ethylene oxide with fatty alcohols or with alkyl phenols.

It can also be advantageous to use surfactants having a perfluorinated hydrophobic chain, such as, for example, ammonium perfluorooctanoate or potassium N-perfluorooctylsulphonyl-N-ethylaminoacetate.

To facilitate the emulsification of the monomers, it is generally necessary to use organic solvents such as, for example, ketones (acetone, methyl ethyl ketone, methyl isobutyl ketone), glycols or ethylene glycol ethers, alcohols (methanol, ethanol, isopropanol), or mixtures of these solvents. The amount of solvent should not generally exceed the total weight of the monomers.

As initiators of polymerization in aqueous emulsion, it is possible to use water-soluble products, such as inorganic peroxides (for example hydrogen peroxide) and persalts (for example potassium persulphate), or initiators which are insoluble in water such as organic peroxides and the azo compounds mentioned above.

The fluorinated polymers according to the invention can also be prepared by grafting a fluorinated urethane-isocyanate of formula (IV) onto an acrylic polymer having pendent OH groups, which is obtained by homopolymerization of an acrylic ester of formula (V) or by copolymerization of such an ester with one or more of the comonomers mentioned above. The grafting operation can be carried out under the same conditions as the addition of ester (V) to the fluorinated urethane-isocyanate (IV). The acrylic polymer having pendent OH groups can itself be obtained by polymerization in a solvent medium under conditions similar to those described above for the polymerization of the monomers of formula (II).

Regardless of the method by which they are obtained, the fluorinated polymers according to the invention can optionally be isolated according to methods known per se, such as, for example, precipitation or evaporation of the solvent.

The fluorinated polymers according to the invention prove to be excellent hydrophobic and oleophobic agents on very diverse materials such as paper, nonwoven articles, textiles based on natural, artificial or synthetic fibers, plastics, wood, metals, glass, stone and cement, but are intended especially for the protection of leathers, both for the finishing thereof and for the maintenance of leather articles such as clothing, shoes, fancy leather goods, seats, etc.

For application, the solutions of polymers are generally diluted with a solvent identical to or compatible with that used for the polymerization, while the emulsions of polymers are diluted with water. The application of the dilute products can be carried out according to different techniques, such as spraying, brush-coating and padding. Depending on their nature, the substrates treated can be dried at room temperature or at temperatures which can range up to 200° C.

The amount of polymer to be employed can vary within wide limits, depending on the nature of the support and the fluorine content of the polymer. On leather, this amount is generally within the range of about 1 to 10 g/m².

The examples which follow, in which the parts and percentages are understood to be by weight, except

EXAMPLE 1

A reactor of capacity 1,000 parts by volume, equipped with a stirrer, a thermometer, a reflux condenser, a dropping funnel, a nitrogen inlet and a heating device, is charged with 90 parts of trichlorotrifluoroethane and 8.7 parts of pure toluene 2,4-diisocyanate (0.05 mole). The air is driven out of the reactor with a stream of dry nitrogen, the solution is then brought to reflux (50° C.) and a solution of 18.2 parts of 2-perfluoro-hexylethanol $C_6F_{13}C_3H_4$ (0.05 mole) and 0.1 part of dibutyltin dilaurate in 20 parts of trichlorotrifluoroethane is then introduced dropwise in the course of two hours. The fine white suspension thereby obtained is maintained at 50 C for a further ½ hour. Chromatographic analysis (LC) then shows the complete disappearance of the fluorinated alcohol and the formation, besides the 2-isocyanate-4-urethane, of the symmetrical 2,4-diaddition product (molar proportion: 20%).

A solution of 6.5 parts of 2-hydroxyethyl methacrylate (0.05 mol) in 10 parts of trichlorotrifluoroethane is then added dropwise, and refluxing is maintained for one hour. After evaporation of the solvent, 33 g are obtained of a mixture of diurethane monomer and symmetrical diaddition product, which is removed by fractional crystallization in toluene. A colorless syrupy liquid is obtained, the ($^1$H and $^{13}$C) NMR analysis of which confirms the expected structure:

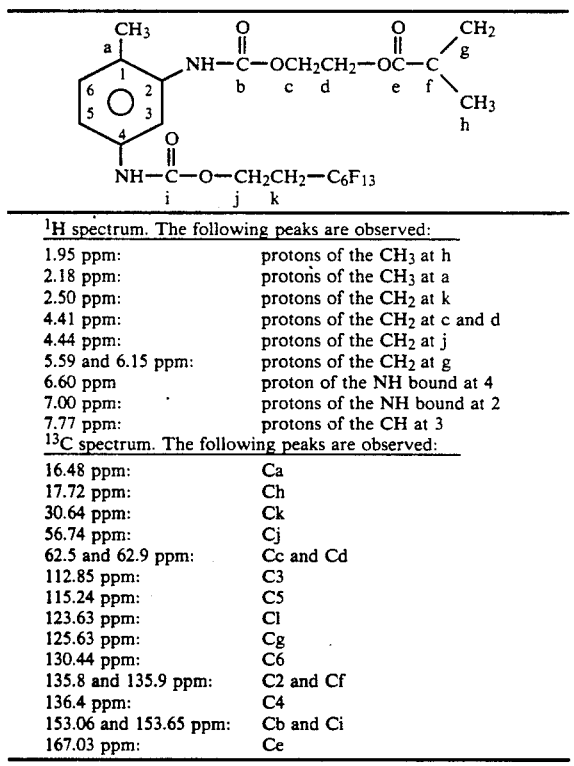

| $^1$H spectrum. The following peaks are observed: | |
|---|---|
| 1.95 ppm: | protons of the $CH_3$ at h |
| 2.18 ppm: | protons of the $CH_3$ at a |
| 2.50 ppm: | protons of the $CH_2$ at k |
| 4.41 ppm: | protons of the $CH_2$ at c and d |
| 4.44 ppm: | protons of the $CH_2$ at j |
| 5.59 and 6.15 ppm: | protons of the $CH_2$ at g |
| 6.60 ppm | proton of the NH bound at 4 |
| 7.00 ppm: | protons of the NH bound at 2 |
| 7.77 ppm: | protons of the CH at 3 |
| $^{13}$C spectrum. The following peaks are observed: | |
| 16.48 ppm: | Ca |
| 17.72 ppm: | Ch |
| 30.64 ppm: | Ck |
| 56.74 ppm: | Cj |
| 62.5 and 62.9 ppm: | Cc and Cd |
| 112.85 ppm: | C3 |
| 115.24 ppm: | C5 |
| 123.63 ppm: | C1 |
| 125.63 ppm: | Cg |
| 130.44 ppm: | C6 |
| 135.8 and 135.9 ppm: | C2 and Cf |
| 136.4 ppm: | C4 |
| 153.06 and 153.65 ppm: | Cb and Ci |
| 167.03 ppm: | Ce |

EXAMPLE 2

A reactor of capacity 500 parts by volume, equipped with a stirrer, a thermometer, a reflux condenser, a dropping funnel, a nitrogen inlet and a heating device, is charged with 127 parts of anhydrous methyl isobutyl ketone, and 17.4 parts (0.1 mole) of toluene diisocyanate (mixture containing 80% of 2,4-isomer and 20% of 2,6 (isomer) and 0.1 part of dibutylin dilaurate. The air is driven out of the reactor with a stream of dry nitrogen, the temperature of the reaction medium is then brought to 80° C. using a thermostated oil bath and a previously topped solution comprising 36.4 parts (0.1 mole) of 2-perflourohexyl-ethanol $C_6F_{13}C_2H_4OH$ and 36.4 parts of methyl isobutyl ketone is then introduced dropwise in the course of one hour and a half. After the mixture has been maintained at 80° C. for a further 30 minutes, a chemical assay shows that half of the —NCO groups has effectively reacted. A liquid chromatographic analysis shows the formation, besides the 2-isocyanate-4-urethane, of an approximately 20% molar proportion of symmetrical 2,4-diaddition product.

0.06 part of hydroquinone methyl ether is then added, 13 parts (0.1 mole) of 2-hydroxyethyl methacrylate are then introduced dropwise in the course of 15 minutes and the mixture is then maintained at 80° C. for a further hour. Chromatographic analysis shows that no 2-hydroxyethyl methacrylate remains. The solution is then filtered at about 35° C., and then cooled. A solution ($S_2$) is thereby obtained of a mixture of monomer according to the invention and symmetrical diurethane which it is unnecessary to separate. This solution consists of 29% of dry matter and 10.73% of fluorine.

EXAMPLE 3

The procedure is as in Example 2, but with the solution of perfluorohexylethanol replaced by a solution of 46.4 parts of perfluorooctylethano $C_8F_{17}C_2H_4$ in 46.4 parts of methyl isobutyl ketone. The degree of conversion to the diaddition product is slightly greater (approximately 30%). A solution ($S_3$) is obtained which partially crystallizes in the cold and contains 29% of dry matter and 12.2% of fluorine.

EXAMPLE 4

The procedure is as in Example 2, but with the solution of perfluorohexylethanol replaced by a solution of 48.5 parts of the fluorinated sulphamido alcohol of formula $C_6F_{13}C_2H_4SO_2N(CH_3)C_2H_4OH$ in 48.5 parts of methyl isobutyl ketone. The degree of conversion to the symmetrical 2,4-diaddition product is 40%. A solution ($S_4$) is obtained which partially crystallizes in the cold and which contains 29% of dry matter and 9% of fluorine.

EXAMPLE 5

The procedure is as in Example 2, but with the solution of perfluorohexylethanol replaced by a solution of 48 parts of the fluorinated thiol $C_8F_{17}C_2H_4SH$ in 48 parts of methyl isobutyl ketone. The molar level of symmetrical diaddition product is 24%. A solution ($S_5$) is obtained which partially crystallizes in the cold and which contains 29% of dry matter and 11.9% of fluorine.

EXAMPLE 6

The procedure is as in Example 2, but with the 2-hydroxyethyl methacrylate replaced by 11.6 parts of 2-hydroxyethyl acrylate (0.1 mole). The solution ($S_6$) obtained contains 24.6% of dry matter and 9.3% of fluorine.

EXAMPLE 7

The procedure is as in Example 2, but with the 2-hydroxyethyl methacrylate replaced by 13 parts of 2-hydroxypropyl acrylate (0.1 mole). The solution ($S_7$) obtained contains 25% of dry matter and 9.25% of fluorine.

EXAMPLE 8

The procedure is as in Example 2, but with the 2-hydroxyethyl methacrylate replaced by 14.4 parts of 4-hydroxybutyl acrylate (0.1 mole). The solution ($S_8$) obtained contains 29% of dry matter and 10.5% of fluorine.

EXAMPLE 9

A reactor of capacity 250 parts by volume, equipped with a stirrer, thermometer, reflux condenser, a nitrogen inlet and a heating device, is charged with 125 parts of the solution ($S_2$), flushing with nitrogen is then performed at the surface for 15 minutes and the temperature is brought to 0° C.. 0.3 part of lauroyl peroxide and 0.2 part of t-butyl perpivalate are then added. The temperature is then maintained at 90° C. for 6 hours, the same charge of initiators being added again after 2 and 4 hours. After the mixture is cooled, a clear yellow solution is obtained of a homopolymer according to the i This solution contains 29% of dry matter and 10.7% of fluorine.

Working in the same manner with the solutions $S_3$, $S_4$, $S_5$, $S_6$, $S_7$ and $S_8$ of Examples 3 to 8, there are obtained, respectively, solutions $S_{3p}$ to $S_{8p}$ of homopolymers according to the invention.

Each of the solutions $S_{2p}$ to $S_{8p}$ is diluted with methyl isobutyl ketone so as to obtain solutions each containing 0.20% of fluorine. These dilute solutions are then applied by spraying on a vegetable-tanned full-grain kip leather, in the proportion of 200 g/m², and the leather is left to dry overnight at room temperature before the following tests are carried out:

WR Test (water resistance): consists in measuring the time for penetration of a drop of water deposited on the leather.

OR Test (Oil resistance)- consists in measuring the time for penetration of a drop of liquid paraffin deposited on the leather.

The table which follows collates the results obtained, in comparison with the same leather untreated.

| Treatment Solution | Hydrophobic effect WR | Oleophobic effect OR |
|---|---|---|
| None (untreated Leather) | Less than 30 seconds | Less than 10 seconds |
| $S_{2p}$ | 7.3 hours | 45 minutes |
| $S_{3p}$ | 4 hours | more than 30 hours |
| $S_{4p}$ | 3.5 hours | more than 30 hours |
| $S_{5p}$ | 8 hours | more than 30 hours |
| $S_{6p}$ | 1.75 hours | 30 minutes |
| $S_{7p}$ | 0.5 hour | 30 minutes |
| $S_{8p}$ | 1.75 hour | 5 hours |

EXAMPLE 10

A reactor of capacity 1,000 parts by volume, equipped in the same manner as that of Example 9, is charged with 310.3 parts of the solution ($S_2$), 50 parts of methyl isobutyl ketone and 90 parts of 2-ethylhexyl methacrylate. After the system has been flushed with nitrogen, the temperature is brought to 90° C., 0.3 parts of lauroyl peroxide and 0.2 parts of t-butylperpivalate are then added and the temperature is then maintained at 90° C. for 6 hours, the same amount of initiators being added again every two hours.

The clear yellow solution of copolymer ($S_{10}$) thereby obtained contains 40% of non-volatile matter and 7.5% of fluorine.

EXAMPLE 11

Under conditions identical to those of Example 10, 310.3 parts of solution ($S_2$), 30.6 parts of 2-ethylhexyl methacrylate and 59.4 parts of 2-perfluorohexylethyl methacrylate are copolymerized in 50 parts of methyl isobutyl ketone.

The solution of copolymer thereby obtained ($S_{11}$) is clear and contains 39.1% of non-volatile matter and 14.6% of fluorine.

EXAMPLE 12

The procedure is as described in Example 10, but only 36 parts of 2-ethylhexylmethacrylate are used, the remainder being replaced by 54 parts of a mixture of polyfluorinated acrylic monomers of formula:

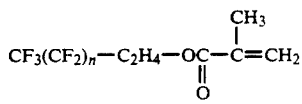

where n equals 5, 7, 9, 11, 13 and 15 in average ratios by weight, respectively, of 47:32:13:5:2:1.

The solution of copolymer thereby obtained ($S_{12}$) is yellow, clear and slightly viscous. It contains 38.8% of non-volatile matter and 14.1% of fluorine.

EXAMPLE 13

According to the same procedure as in Example 10, 310.3 parts of solution ($S_2$), 16.2 parts of 2-ethylhexyl methacrylate and 73.8 parts of a mixture of fluorinated acrylic esters of formula:

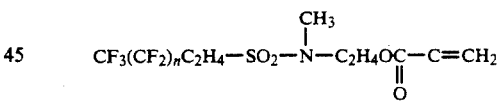

where n equals 3, 5, 7, 9, 11, 13 and 15 in the average ratios by weight, respectively, of 1:50:31:10:3:1:1, are copolymerized in 25 parts of methyl isobutyl ketone and 25 parts of acetone. A clear, yellow-brown solution ($S_{13}$) is obtained, containing 40.6% of non-volatile matter and 15.1% of fluorine.

EXAMPLE 14

Working as in the first paragraph of Example 9, 86.2 parts of solution , 10 parts of 2-ethylhexyl methacrylate and 15 parts of the same mixture of polyfluorinated acrylic monomers as in Example 12 are copolymerized.

The copolymer ($S_{14}$) thereby obtained takes the form of a gelatinous mass in which the level of dry matter is 40.1% and the fluorine level is 14.5%.

EXAMPLE 15

Working as in Example 9, 69 parts of solution ($S_3$), 5 parts of 2-ethylhexyl methacrylate and 25 parts of a mixture of polyfluorinated monomers of formula:

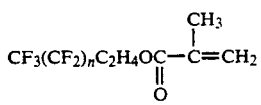

where n equals 5, 7, 9, 1 1, 13 and 15 in average ratios by weight, respectively, of 1:56:22:9:3:3, are copolymerized in 25 parts of methyl isobutyl ketone. When the polymerization is complete, the mixture is diluted with 125 parts of trichlorotrifluoroethane.

A clear amber-colored solution is obtained containing 18.8% of non-volatile matter and 9% of fluorine.

EXAMPLE 16

90 parts of methyl isobutyl ketone, 55 parts of stearyl methacrylate and 5 parts of 2-hydroxyethyl methacrylate are introduced into a reactor of capacity 500 parts by volume, equipped with a stirrer, a thermometer, a reflux condenser and a nitrogen inlet. The mixture is heated under an atmosphere of nitrogen for 1 h 30 min at 80° C. in the presence of 0.4 part of lauroyl peroxide and 0.25 part of t-butyl perpivalate. Chromatographic assay shows a degree of polymerization of 70%.

92.7 parts of a solution of urethane-isocyanate, obtained by working in the same manner as in the first paragraph of Example 2, are then added. The mixture is then heated to 80° C. for 4 hours, adding 0.4 part of lauroyl peroxide and 0.2 part of t-butyl perpivalate.

The graft copolymer ($S_{16}$) thereby obtained takes the form of a thick amber-colored solution in which the level of dry matter is 37.7% and the fluorine level is 4.7%.

EXAMPLE 17

17-a: 34.7 parts of butyl methacrylate, 39 parts of the same mixture of polyfluorinated monomers as in Example 15 and 13 parts of 2-hydroxyethyl methacrylate are copolymerized in 87 parts of methyl isobutyl ketone in a reactor identical to that of Example 16. The procedure is carried out under an atmosphere of nitrogen and at 100° C for 6 hours, initially adding 1 part of lauroyl peroxide and 0.2 part of t-butyl perpivalate and repeating this addition of initiators after 2 and 4 hours.

17-b: 88 parts of methyl isobutyl ketone, 17.4 parts of toluene diisocyanate (containing 80% of 2,4-isomer) and 0.1 part of dibutyltin dilaurate are introduced into a reactor identical to that of Example 2. After the air has been driven out of the reactor with a stream of dry nitrogen, the temperature is brought to 80° C., and 36.4 parts of perfluorohexylethanol dissolved in 36.4 parts of methyl isobutyl ketone are then introduced dropwise in the course of one hour. The mixture is maintained at 80° C. for a further hour, all of the hydroxylated copolymer synthesized in stage 17-a is then added and the mixture is brought to 100° C. for 4 hours.

A rather viscous solution is thereby obtained which contains 39.7% of non-volatile matter and 13.8% of fluorine.

EXAMPLE 18

The procedure is as in Example 2 for reacting perfluorohexylethanol $C_6F_{13}C_2H_4OH$ with toluene diisocyanate. A mixture of 6.5 parts of 2-hydroxyethyl methacrylate (0.05 mole) and 9.25 parts of 2-t-butyl-amino-ethyl methacrylate (0.05 mole) is then added dropwise in the course of ¼ hour at 80° C. The mixture of diurethane and urethane-urea monomers thereby obtained is copolymerized at 90° C. in the presence of 0.5 part of lauroyl peroxide and 0.4 part of t-butyl perpivalate, added every two hours for six hours.

A yellow-brown solution ($S_{18}$) is obtained, containing 29.1% of dry matter and 10.35% of fluorine.

The solutions $S_{10}$, $S_{11}$, $S_{12}$, $S_{13}$, $S_{14}$, $S_{15}$, $S_{16}$, $S_{17}$ and $S_{18}$ of the above examples are diluted with methyl isobutyl ketone so as to obtain solutions $S_{10d}$ to $S_{18d}$ containing 0.4% of fluorine. These dilute solutions are then applied by spraying on a vegetable-tanned full-grain kip leather in the proportion of 200 g/m² and the leather is left to dry overnight at room temperature before the same tests are carried out as in Example 9. The results obtained are collated in the following table:

|  | Hydrophobic effect WR | Oleophobic effect OR |
|---|---|---|
| Untreated Leather | Less than 30 seconds | Less than 10 seconds |
| Leather treated with: |  |  |
| $S_{10d}$ | 6.5 hours | more than 30 hours |
| $S_{11d}$ | 6.5 hours | more than 30 hours |
| $S_{12d}$ | 7.5 hours | more than 30 hours |
| $S_{13d}$ | 8 hours | more than 30 hours |
| $S_{14d}$ | 9 hours | more than 30 hours |
| $S_{15d}$ | 4.5 hours | more than 30 hours |
| $S_{16d}$ | 7.75 hours | more than 30 hours |
| $S_{17d}$ | more than 9 hours | more than 30 hours |
| $S_{18d}$ | more than 9 hours | more than 30 hours |

EXAMPLE 20

220 parts of previously topped butyl acetate, 34.8 parts (0.2 mole) of toluene-diisocyanate (mixture containing 80% of 2,4-isomer and 20% of 2,6-isomer) and 0.2 parts of dibutyltin dilaurate are charged into a reactor identical to that of Example 1. Air in the reactor is driven out with a stream of dry nitrogen, the temperature is then brought to 80° C. with the aid of a thermostated oil bath and a solution of 72.8 parts (0.2 mole) of 2-perfluorohexyl-ethanol $C_6F_{13}C_2H_4OH$ in 72.8 parts of dry butyl acetate is then added in the course of two hours.

0.12 parts of hydroquinone methyl ether is then added and a solution of 26 parts (0.2 mole) of 2-hydroxyethyl methacrylate in 26 parts of dry butyl acetate is then introduced in the course of 15 minutes. After the mixture has been maintained at 80° C. for one hour, 35.6 parts of 2-ethylhexyl methacrylate, 8.9 parts of 2-hydroxyethyl methacrylate and 100 parts of butyl acetate are added. The temperature is brought to 90° C., then 1 part of lauroyl peroxide and 0.7 part of tert-butyl perpivalate are added. After 3 hours, the polymerization has ended and a terpolymer according to the invention is thus obtained which has the form of a clear light yellow solution containing 30% of non-volatile matter and 8.3% of fluorine.

Solution $S_{20}$ is diluted with isopropanol so as to obtain a solution containing 0.4% of fluorine which is applied in the conditions described in Example 19. The results are as follows:
WR : more than 9 hours
OR : more than 30 hours While it is apparent that the invention herein disclosed is well calculated to fulfill the desired results, it will be appreciated that numerous modifications and embodiments may be devised by those skilled in the art, and it is intended that the appended claims cover all such modifications embodiments as fall within the true spirit and scope of the present invention.
What is claimed is:
1. A fluorinated acrylic monomer of the formula:
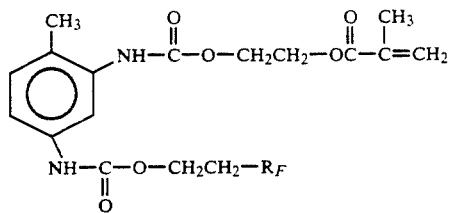
in which $R_F$ denotes a perfluoroalkyl radical containing from 4 to 16 carbon atoms.
2. The fluorinate acrylic monomer of claim 1 where $R_F$ is $C_6F_{13}$.
* * * * *